United States Patent
Boschetti et al.

(10) Patent No.: US 6,972,090 B2
(45) Date of Patent: Dec. 6, 2005

(54) COMPOSITE CHROMATOGRAPHIC SORBENT OF MINERAL OXIDE BEADS WITH HYDROXYAPATITE-FILLED PORES

(75) Inventors: Egisto Boschetti, Croissy sur Seine (FR); Pierre Girot, Paris (FR)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 10/305,399

(22) Filed: Nov. 27, 2002

(65) Prior Publication Data

US 2003/0125529 A1    Jul. 3, 2003

Related U.S. Application Data

(60) Provisional application No. 60/333,149, filed on Nov. 27, 2001.

(51) Int. Cl.$^7$ ............................................. B01D 15/08
(52) U.S. Cl. ............................... 210/198.2; 210/502.1; 502/400; 502/405; 502/414
(58) Field of Search ........................... 210/502.1, 656, 210/198.2; 502/400, 405, 414

(56) References Cited

U.S. PATENT DOCUMENTS

| | | | |
|---|---|---|---|
| 3,954,678 A * | 5/1976 | Marquisee | 252/62.54 |
| 5,114,577 A * | 5/1992 | Kusano et al. | 210/198.2 |
| 5,158,756 A | 10/1992 | Ogawa et al. | |
| 5,240,601 A * | 8/1993 | Mazid | 210/198.2 |
| 5,561,884 A | 10/1996 | Nijland et al. | |
| 5,567,231 A | 10/1996 | Yokoo et al. | |
| 5,651,884 A * | 7/1997 | Ichitsuka et al. | 210/198.2 |
| 5,906,747 A * | 5/1999 | Coffman et al. | 210/635 |
| 6,572,766 B1 * | 6/2003 | Bergstrom et al. | 210/198.2 |
| 6,613,234 B2 * | 9/2003 | Voute et al. | 210/656 |

FOREIGN PATENT DOCUMENTS

| | | | |
|---|---|---|---|
| JP | 62-206445 | 9/1987 | |
| JP | 62-230607 | 10/1987 | |
| WO | WO 99/51335 | * 10/1999 | 210/198.2 |

OTHER PUBLICATIONS

Tiselius et al.; "Protein Chromatography on Calcium Phosphate Columns"; Archives of Biochemistry and Biophysics, 65, (1956), pp. 132-155.
Matsumoto et al.; "Inhibiting Action of Carbohydrates on the Growth of Fluorapatite Crystals", Carles Research 2000, 34:26-32.
Okazaki et al.; "Functionally graded fluoridated apalites" Biomaterials 20 (1999) 1421-1426.
Okazaki et al.; "Differences in soloubility of two types of heterogeneous fluoridated hydroxyapatites", Biomaterials 19 (1998) 611-616.

* cited by examiner

Primary Examiner—Ernest G. Therkorn
(74) Attorney, Agent, or Firm—Leydig, Voit & Mayer, Ltd.

(57) ABSTRACT

A new adsorbent of a porous mineral oxide material with apatite crystals, preferably hydroxyapatite crystals, in the pores of the mineral oxide material is disclosed. The adsorbent is useful for protein and nucleic acid separations

14 Claims, No Drawings

COMPOSITE CHROMATOGRAPHIC SORBENT OF MINERAL OXIDE BEADS WITH HYDROXYAPATITE-FILLED PORES

BACKGROUND OF THE INVENTION

The present invention relates to a new adsorbent of a porous mineral oxide material with apatite crystals, preferably hydroxyapatite crystals, in the pores of the mineral oxide material. The adsorbent is useful for protein and nucleic acid separations.

Apatite is a calcium phosphate material in crystalline form having the general formula $Ca_5(F, Cl, OH, ½ CO_3)(PO_4)_3$. One of the more common types of apatite is hydroxyapatite which has the formula $[Ca_2(PO_4)_2]_3Ca(OH)_2$. It is useful as a packing material to be filled in columns for chromatographic separation of biopolymers, for example, proteins, enzymes, and nucleic acids. Its ability to adsorb such molecules depends on both the structure of the crystal itself and on the exposed surface area of the crystals.

The technique for the preparation of hydroxyapatite utilizable for column chromatography was first developed by Tiselius et al. [*Arch. Biochem. Biophys.*, 65:132–155 (1956)]. Hydroxyapatite for column chromatographic use has been prepared by various methods. Conventionally, hydroxyapatites are synthesized by (1) wet synthesis in which a water-soluble calcium salt and phosphate are allowed to react in aqueous solution, (2) dry synthesis in which calcium phosphate and calcium carbonate are allowed to react in the presence of water vapor at 900° to 1400° C., or (3) hydrothermal synthesis in which calcium hydrogen-phosphate is hydrolyzed, for example, at 200° C. and 15 atmospheres. The hydroxyapatites produced in conventional processes have been in the form of plates which have to be finely divided, particularly when used as column packing material for chromatographic separation. The plates are divided into tiny pieces varied in shape and size. The irregular pieces of hydroxyapatite cannot be packed uniformly or densely in the column for chromatographic separation.

Hydroxyapatite in the form of plate-like crystals or agglomerates of microcrystals also is inferior in mechanical strength and tends to be destroyed during the packing operation and measurement. Chromatographic characteristics of the hydroxyapatite vary according to the packing method used, leading to variability in separations and bed collapse.

In recent years, a process for producing microspherical hydroxyapatite was proposed to overcome these shortcomings, utilizing the so-called spray-drying method which is widely used for manufacturing granules of a powdery substance (Japanese Laid-open Patent Appln. Nos. Sho. 62-206445 and 62-230607). According to the process disclosed in Japanese Laid-open Patent Appln. No. 62-206445, microcrystals of hydroxyapatite having a diameter of less than 1 μm as primary particles are physically coagulated by spray drying to form substantially spherical particles of 1–10 μm in diameter as second particles.

When the spherical hydroxyapatite particles obtained according to these processes are subjected to classification by screening to collect particles of a definite particle size as a packing material for liquid chromatography, the spherical particles tend to be destroyed because of their poor mechanical strength and are broken to pieces when packed densely in a column under high pressure. Consequently, the spherical hydroxyapatite particles formed by spray drying have to be subjected to a heat treatment carried out at a high temperature for a long period of time in order to impart mechanical strength sufficient enough to withstand high pressure on packing. The severe heat treatment, however, causes the spherical particles tend to be bonded to one another in a mutually fused state to form partially solid state granules.

Japanese Laid-open Patent Appln. No. Sho. 62-230607 discloses a process for preparing spherical agglomerates of apatite in which a gelled hydroxyapatite slurry is sprayed into an atmosphere kept at 100–200° C. to form spherical agglomerates of hydroxyapatite having a diameter of 1–10 μm. Hydroxyapatite trapped in a hydrogel network is relatively soft, and binding capacity is modest because of the limited amount of hydroxyapatite crystals present in a given volume of sorbent, about 40%. The presence of a hydrogel that surrounds crystals of hydroxyapatite prevents the direct contact with very large molecules such as plasmids.

Thus, the conventional processes involve a number of problems not only in the preparation of spherical hydroxyapatite particles but also in the use of the particles as a packing material for chromatographic purposes.

Mineral oxide beads for use in chromatography are known, and can have more strength than hydroxyapatite sorbents. For applications in which another substance is introduced into the bead, a pore size larger than 500 Å is required to allow for unhindered diffusion of large molecules. It is difficult to obtain a large pore diameter, however, without adversely affecting porosity and strength. Moreover, mineral oxide surfaces exhibit various types of interactions with proteins, including electrostatic, van der Waals, and Lewis acid-base, that can alter the quality of a separation or even denature a biomolecule.

There is a need for relatively small porous particles which provide the separation capabilities of apatite yet retain their shape, their chemical and mechanical properties in specific environments useful for biomolecule separation in columns as well as in suspensions, and which offer a substantial density difference with liquids used in adsorption and chromatography. Such apatite materials excellent in mechanical strength and chromatographic characteristics have not, as yet, been described.

SUMMARY OF THE INVENTION

In accordance with the present invention, a chromatography sorbent is provided which combines the separation capabilities of hydroxyapatite crystals with the strength of a mineral oxide network. This composite sorbent exhibits superior properties when used in chromatographic separation, or in substance separation or development when used as the adsorbent packed or charged into a column or as a stationary phase agent in column chromatography. Chromatography using this sorbent as the adsorbent in batch separations or packed in either a fixed bed or fluidized bed column achieves high acuteness and precision separation and fractionation of substances having a minute difference in structure from one another. This was difficult to achieve with the use of prior-art adsorbents. Such substances may include biological macromolecule materials having a molecular weight of $10^4$ to $10^9$ Dalton, such as proteins, including immunoglobulins, interferon or enzymes, or nucleic acids, such as RNA, DNA or plasmids or viruses. The composite sorbent is indispensable for high purity separation and refining of a variety of ultimately useful substances obtained by gene recombination, cell fusion or cell culture en masse.

The composite chromatographic sorbent comprises mineral oxide beads with pores filled with apatite, particularly hydroxyapatite. The mineral oxide beads of the composite sorbent are characterized by high porosity, low surface area, high mean pore diameter, and high mechanical stability. Moreover, they show a density that facilitates packing of fixed-bed columns, increases the particle sedimentation velocity in batch, and permits the use of high velocity in fluidized-bed operations. The apatite crystals are protected by a very strong skeleton of mineral oxide, preferably zirconia.

Specifically, the present invention encompasses a composite chromatography sorbent comprising porous mineral oxide beads that have a pore volume which exceeds about 10% of the bead volume, preferably about 30% and about 70%, and more preferably about 30% and about 60%, and an average pore diameter of at least about 500 Å, preferably between about 1000 Å and about 4000 Å, and more preferably between about 1000 Å and about 3000 Å. The pores of the beads contain apatite, and preferably hydroxyapatite, crystals. Preferably, the mineral oxide is selected from the group consisting of alumina, titania, hafnia, silica, zirconia and mixtures thereof, and most preferably it is zirconia. In a preferred embodiment, the mineral is silica, the pore volume is between about 40% and about 70% of the bead volume, and the average pore diameter is between about 2000 Å and about 5000 Å.

In one embodiment, the beads of the composite chromatography sorbent are coated with a layer of hydrophilic polymer, preferably a hydrophilic polymer selected from the group consisting of polyoxyethylene, polyoxypropylene, cross-linked polysaccharides and vinyl polymers.

In a preferred embodiment, the apatite crystals comprise calcium ions and a metal ion or a metalloid ion. Preferably, the metal ion or metalloid ion is strontium, barium or fluoride.

The present invention also encompasses chromatography apparatus and methods. A chromatography column comprises a tubular member having an inlet end and an outlet end; first and second porous members disposed within the tubular member; and a composite chromatography sorbent according to the invention packed within the tubular member between the first and second porous members. Preferably, the column volume is between about 50 liters and about 5000 liters. The column additionally may comprise means for flowing a liquid sample upward through the composite chromatography sorbent.

The column may be used in a chromatographic separation method comprising flowing a solution comprising biomolecules through the chromatography column so that the solution permeates the pores of the mineral oxide beads, wherein some biomolecules in the solution are bound to the apatite crystals and other, different biomolecules remain in the solution. This may be followed by flowing another solution through the chromatography column to elute the biomolecules bound to the apatite crystals. In one embodiment the biomolecules are polypeptides, and in another embodiment the biomolecules are nucleic acids. Substances other than proteins and nucleic acids are included within the scope of the term biomolecule, such as glycopeptides.

The composite sorbent may also be used in batch chromatography apparatus and methods. In a batch method, a solution comprising biomolecules is brought into contact with the composite chromatography sorbent, so that the solution permeates the pores of the mineral oxide beads, wherein some biomolecules in the solution are bound to the apatite crystals and other, different biomolecules remain in the solution.

The present invention also provides a method of making a composite chromatography sorbent according to the invention, comprising: (1) providing porous mineral oxide beads that have a pore volume which exceeds about 10% of the bead volume and an average pore diameter of at least about 500 Å; (2) contacting the porous mineral oxide beads with a maximum of one pore volume of a solution of either (i) calcium chloride or (ii) potassium or sodium phosphate so that it permeates the pores of the beads; (3) drying the beads; (4) contacting the dried beads with a maximum of one pore volume of a solution of the other of either (i) calcium chloride or (i) potassium or sodium phosphate so that it permeates the pores of the beads, thereby forming calcium phosphate in the pores; (5) washing the beads with water to eliminate excess calcium or phosphate ions; (6) contacting the washed beads with a solution of sodium hydroxide; (7) washing the beads with water; and (8) contacting the washed beads with a solution of disodium phosphate to form hydroxyapatite crystals in the pores of the beads. In a preferred embodiment, the beads are washed with a phosphoric acid solution before contacting the porous mineral oxide beads with a maximum of one pore volume of a solution of either (i) calcium chloride or (ii) potassium or sodium phosphate.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF PREFERRED EMBODIMENTS

The composite chromatography sorbent according to the invention uses mineral oxide beads to impart mechanical stability to an apatite sorbent. The mineral oxide beads have a pore volume of at least about 10% of the bead volume and an average pore diameter of at least about 500 Å.

In a preferred embodiment, mineral oxide beads with a higher pore volume, preferably at least about 30%, more preferably at least about 40%, and most preferably at least about 50%, are used. The preparation of mineral oxide beads having high pore volumes is described in WO 99/51335, the contents of which are incorporated herein in their entirety. The beads can be small discrete beaded particles as well as irregular shaped particles, showing high pore volume and high mechanical and chemical stability. Because of their stability and high porosity, they are particularly useful in packed bed, fluidized bed or stirred batch adsorption or chromatographic separation for large macromolecules.

The mineral oxide beads are prepared by combining a tetravalent metal oxide with a trivalent metal salt or oxide as a pore inducing agent. The combination results in the formation of unstable suspensions which, after agglomeration to form spherical or irregular particles, show both macroporosity and large pore sizes. The porosity and pore size is greater than that which can be obtained in the absence of the trivalent metal salt or oxide.

The mineral oxide preferably is an oxide of titania, zirconia, silica or hafnium, preferably silica or zirconia, and most preferably zirconia. The mineral oxide can also be a mixture of two or more tetravalent metal oxides. Preferably the mineral oxide powders are in the form of a powder, and most preferably a powder with a particle size of about 0.1 to about 10 μm.

The trivalent metal can be used in the form of an oxide, a salt, or mixtures of oxide and salt. A particularly preferred salt is nitrate. The metal can be any metal which exhibits a +3 valence, such as Group IIIB metals, rare earth metals, and the like. Preferred trivalent metals are aluminum, gallium, indium, scandium, yttrium, lanthanum, cerium, neodymium, erbium, ytterbium and actinium. Also included are compositions in which the trivalent metal oxide or salt is a mixture of two or more such oxides or salts. Such mixtures include salt/oxide, salt/salt, and oxide/oxide mixtures of the same or different trivalent metals.

Only a limited pore volume reduction is observed when firing the compositions at very high temperatures. In contrast, mineral oxide beads obtained without the use of the trivalent metal salt or oxide have lower pore volumes when fired at very high temperatures, due to a severe reduction of pore volume resulting from the firing process. The trivalent metal salt or oxide additionally stabilizes a crystalline form of the mineral oxide and prevents grain growth and cracking of the final material.

Optionally, an agent that induces particle agglomeration to make a beaded final material, such as an agglomeration promoting material or a binder, may be included. These may be salts of trivalent or tetravalent metals, and can contain the same tetravalent or trivalent metals just described. In a preferred embodiment, the binder comprises a mixture of nitrates, including a tetravalent metal nitrate and trivalent metal nitrate. For example, when zirconium oxide is used as a mineral oxide bead constituent and cerium oxide is used as the trivalent pore inducing agent, it is convenient to use a mixture of zirconium nitrate and cerium nitrate as a binder. Other suitable binders include materials which form mineral hydrogels that can encapsulate mineral oxide elemental particles, for example, silica gels. A mineral hydrogel may also be used in combination with one or more additional binders.

Composite mineral oxides with enhanced pore volume are made by preparing a liquid suspension of a tetravalent mineral oxide. The liquid portion of the suspension can be water or any other appropriate solvent. The mineral oxide should be in the form of a powder, with a particle size of between about 0.1 and about 10 μm, with the particular particle size chosen depending on the desired pore size of the porous particles. This suspension is mixed with one or more pore inducing trivalent agents. The suspension optionally also contains one or more binders.

In a typical composition which includes one or more metal oxide or salt binders, the binders are first mixed in a liquid such as water, then the mineral oxide and the pore inducing agent are added while stirring, producing a suspension. The stirring should be gentle to avoid introducing air bubbles into the mixture.

The amount of pore inducing agent which is used in the initial suspension is roughly proportional to the amount of mineral oxide used. In the final product, the oxide of the tetravalent metal will constitute about 50 to about 99% of the final particles, with the remaining about 1 to about 50% made up of pore inducers and optional binders. In the initial suspension, however, the mineral oxide particles, the major constituent of the porous beads, are at a concentration of about 10 to about 95% by weight, based on the total weight of components used. More preferably, the mineral oxide should be about 20 to about 60% by weight. The pore inducing agent concentration is between about 5 and about 50% by weight. The optimal concentration varies, depending on the nature of the specific compounds used. The concentration of the agglomeration promoting material or binder is between about 0 and about 20% by weight, and also depends on the nature of the binders. Optionally, organic compounds may also be added to the initial suspension in order to alter the viscosity of the solution.

The suspension containing all of the desired components is then used to form beads. A variety of techniques well known in the art, such as spray drying, emulsion-polycondensation and sol-gel processes can be used to effect the agglomeration on the compositions. After the elemental particles are agglomerated into a beaded shape, they are heated at high temperatures to stabilize the architecture of the porous mineral bead by partial fusion of the elemental particles. The heating rate, the calcination temperature and the soak time used depend on the nature of the mineral oxides and mineral pore inducers. A controlled sintering is desirable in order to obtain stronger particles without elimination of the porosity. Typically, temperatures between about 800 and about 1400° C., for a duration of about 1 to about 10 hours, and with a heating rate ranging between about 1 and about 100° C./hour, are used. A sequential calcination treatment also can be used, to first remove volatile components such as water, organic materials, nitrates and the like, and then to sinter the elemental particles.

The fired beads then are cooled to room temperature, and subsequently washed with, for example, acidic, alkaline, neutral or diluted hydro-organic solutions. The particles optionally can be subjected to a sieving step to adjust the particle size distribution, as desired. Typical pore volumes of at least about 30%, about 40% or about 50% can be obtained according to the invention. The upper limit of pore volume is about 70%.

The beads with larger pore volumes and/or average pore diameters are particularly suited for the introduction of apatite crystals, preferably hydroxyapatite, to prepare a composite chromatography sorbent. Pore volume varies based on the bead material. For example, when the mineral oxide is selected from the group consisting of zirconia, titania and hafnia, the pore volume is between about 30% and about 60% of the bead volume. When the mineral is silica and the pore volume is between about 40% and about 70% of the bead volume.

Pore size also varies depending on the bead material, and can be selected based on the material to be separated by the composite sorbent. Larger average pore diameter is selected for applications in separating larger biomolecules, such as plasmids, in which an average pore diameter greater than 2000 Å may be required. The average pore diameter generally is between about 1000 Å and about 4000 Å. When the mineral is selected from the group consisting of zirconia, titania and hafnia, the average pore diameter is between about 1000 Å and about 3000 Å, whereas when the mineral is silica the average pore diameter is between about 2000 Å and about 5000 Å.

In order to fill the pores with hydroxyapatite, mineral oxide beads optionally, but preferably, first are washed with a solution of phosphoric acid to eliminate impurities and then incubated with mono-potassium phosphate. The beads are then washed and dried. If desired, the pore volume can be determined by known methods. The beads are next contacted with a solution of either (i) calcium chloride or (ii) potassium or sodium phosphate, and the solution is allowed to penetrate the pores. The beads are dried and then contacted with a solution of either (i) calcium chloride or (ii) potassium or sodium phosphate. If the beads were contacted with calcium chloride in the first step, then they are contacted with potassium or sodium phosphate in the second step, and vice versa. The solution is allowed to penetrate the pores, and after allowing sufficient time for the calcium phosphate crystalline structure to form within the pores, the beads are washed to eliminate excess calcium or phosphate ions. The beads then are contacted with a solution of sodium hydroxide, and are again washed. Finally, the beads are contacted with a solution of disodium phosphate to form hydroxyapatite crystals in the pores of the beads.

When the mineral beads are contacted with the calcium chloride and potassium or sodium phosphate solutions, it is preferable to use a maximum of one pore volume of solution, and preferably exactly one pore volume. The use of one pore volume exactly generates the maximum amount of hydroxyapatite crystals in the pores of the mineral oxide beads, without having crystals grow outside the pores of the beads.

In an alternative embodiment, the hydroxyapatite made with phosphate ions can be doped with small amounts of other metal ions. The doped metal ions can used to vary the adsorption properties of the composite sorbent.

Apatites other than hydroxyapatite can be grown in the pores. In this case, calcium could be replaced by strontium, barium or other elements. The resulting apatites would have different adsorption properties than hydroxyapatite. Crystalline apatites other than hydroxyapatite, such as apatite derivatives with F, Cl or $CO_3$, are known can be grown in the pores of the mineral oxide beads. For example, the preparation of fluorapatite is described in Matsumoto et al., *Caries Res.*, 34(1):26–32 (2000); Okazaki et al., *Biomaterials*, 20(15):1421–6 (1999); Okazaki et al., *Biomaterials*, 19(10): 919–23 (1998); Okazaki et al., *Biomaterials*, 19(7–9):611–6 (April–May, 1998).

The apatite crystals, and more preferably the hydroxyapatite crystals, comprise calcium ions and a metal ion or a metalloid ion. In embodiments using a metal or metalloid ion, preferred metal ions or metalloid ions is strontium, barium or fluoride.

Prior to the formation of apatite crystals in the pores of the mineral oxide beads, the beads may first be coated with a layer of hydrophilic polymer. Preferably, the hydrophilic polymer is selected from the group consisting of polyoxyethylene, polyoxypropylene, cross-linked polysaccharides and vinyl polymers. The coating reduces non-specific binding for biomolecules.

Different chromatography techniques can be used to separate biomolecules using the composite sorbent according to the invention. These techniques comprise contacting a solution containing the biological macromolecules with the composite sorbent leading to the selective adsorption or molecules in the solution by the sorbent. In the event of the desired macromolecule(s) being fixed to the resin, the elution of the latter allows it or them to be separated and collected in a purified and concentrated form. If the desired macromolecule remains in the treated solution (the other macromolecules being fixed to the sorbent) then the desired separation is obtained directly.

When using batch chromatography, the composite sorbent is added directly to the solution of biomolecules, and the sorbent-biomolecule mixture is gently agitated for a time sufficient to allow the biomolecules to bind to the sorbent. The biomolecule-bound-sorbent may then be removed by centrifugation or filtration, and the biomolecules subsequently eluted in a separate step.

Alternatively, column chromatography may be used. In fixed bed column chromatography, the composite sorbent is packed into a column, and the solution which contains the biomolecules to be separated is applied to the sorbent by pouring it through the sorbent at a rate that allows the biomolecules to bind to the sorbent. Advantages of fixed bed chromatography include minimal column volume and water consumption. The disadvantage of the column chromatography method is that the flow rate of liquids through the column is slow, and, therefore, time-consuming. This flow rate can be reduced even further if the material being applied to the column includes particulates, since such particulate material can "clog" the sorbent to some degree.

In fluidized bed column chromatography, a rising filtration flow and large rather than dense particles are used in order to maintain an equilibrium against the rising forces. An essentially vertical column composed of between 2 and 5 stages placed on top of the other is used, and the solution successively passes through stage and is drawn off by an overflow on the upper part of the upper stage. Each stage, with the exception of the uppermost one, is separated by two perforated distribution systems, one distributing the solution at the base of the stage in question, the other distributing the solution towards the stage located immediately above.

The advantages of a fluidized bed are higher flow rates at lower pressures as compared to fixed bed chromatography. Although the higher flow rates offer certain advantages to the chromatographic separation, the method has several shortcomings. The method requires larger diameter resins that are neutral to gravity or buoyant. These larger diameter sorbents have less surface area per unit volume than smaller sorbents used in fixed bed columns, and correspondingly have less surface binding capacity. The most significant problem of the fluidized bed is mixing. Since the column does not contain any static mixing means, the bed is conventionally mixed by means of air jets or by recycling the liquid to be separated through the column at a high flow rate. The high flow rate and limited mixing inhibit the uniform phase change required during elution of the product from the resin.

On the other hand, fluidized bed chromatography avoids many of the serious disadvantages of fixed beds, which include clogging, need for cleaning, compression and cleaning-induced resin deterioration. In fact, the fluidized bed allows free passage of impurities in the solution with no risk of clogging; no cleaning is necessary so the life-span of the resins is greatly increased. However, the chromatographic sorbents for biological macromolecules typically are not suitable for fluidized bed chromatography, being too small in granulometry, or having a density too close to that of water. This makes it impossible to fluidize without drawing particles into the flux. Another problem with fluidized bed chromatography of biological macromolecules relates to the large space between molecules, would result in a decrease in efficiency in a fluidized bed environment.

Based on these factors, batch and fixed bed chromatography have been the methods of choice in prior art separation techniques for biological macromolecules. The present composite sorbent, on the other hand, can be used in a batch, fixed bed, or fluidized bed chromatography.

The composite sorbent according to the invention is used to separate biomolecules contained in a "source liquid," which is a liquid containing at least one and possibly two or more biological substances or products of value which are sought to be purified from other substances also present. In the practice of the invention, source liquids may for example be aqueous solutions, organic solvent systems, or aqueous/organic solvent mixtures or solutions. The source liquids are often complex mixtures or solutions containing many biological molecules such as proteins, antibodies, hormones, and viruses as well as small molecules such as salts, sugars, lipids, etc. While a typical source liquid of biological origin may begin as an aqueous solution or suspension, it may also contain organic solvents used in earlier separation steps such as solvent precipitations, extractions, and the like. Examples of source liquids that may contain valuable biological substances amenable to the purification method of the invention include, but are not limited to, a culture supernatant from a bioreactor, a homogenized cell suspension, plasma, plasma fractions, milk, colostrum and cheese whey.

The source liquid contains at least one "biomolecule" to be purified from the source liquid. Biomolecules are biological products and include, for example, nucleic acids, immunoglobulins, clotting factors, vaccines, antigens, antibodies, selected proteins or glycoproteins, peptides, enzymes, etc. The biomolecule may be present in the source liquid as a suspension or in solution. For convenience, the term "biomolecule" is used herein in the singular, but it should be understood that it may refer to more than one substance that is to be purified, either together as co-products or separately (e.g., sequentially) as discrete recovered components.

An "elution liquid" or "elution buffer" is used to dissociate the biomolecules, such as glyco-iso-forms, away from the composite sorbent. The elution liquid acts to dissociate the biomolecules without denaturing them irreversibly. Typical elution liquids are well known in the chromatography art and may have higher concentrations of salts, free affinity ligands or analogs, or other substances that promote dissociation of the target substance from the chromatography sorbent. "Elution conditions" refers to process conditions imposed on the biomolecule-bound chromatography sorbent that dissociate the undenatured biomolecules from the chromatography sorbent, such as the contacting of the biomolecule-bound chromatography sorbent with an elution liquid or elution buffer to produce such dissociation.

A "cleaning liquid" or "cleaning buffer" is used to wash the chromatography sorbent after the completion of the separation process. The cleaning liquid may contain a detergent, a virus-inactivating agent, or relatively high concentrations of salts, and may have a higher or lower pH than the liquids used during the purification process. Its purpose is to fully decontaminate the chromatography sorbent to render it ready for reuse. Typical cleaning liquids are well-known in the chromatography art.

Between uses, the composite sorbent is stored in a "storage liquid" or "storage buffer." Storage liquids, in addition to buffering ions, may also contain microbicides or other preservatives. Such storage liquids are well known in the chromatography art.

The composite sorbent can be used in batch separations, or it can be packed into a chromatography column, either a fixed bed or fluidized bed. The column comprises a tubular member having an inlet end and an outlet end, and first and second porous members, such as a glass frit, disposed within the tubular member. The composite chromatography sorbent is packed within the tubular member between the first and second porous members. In a fluidized bed column, there typically are multiple stages. In a preferred embodiment, the column volume is between about 50 liters and about 5000 liters. For fluidized bed chromatography, the column additionally comprises a means for flowing a liquid sample upward through the composite chromatography sorbent.

Batch chromatographic separations comprised mixing the composite sorbent with the source liquid in a suitable container, and gently stirring. Chromatographic separations using column chromatography comprise the steps of flowing a first solution comprising biomolecules through the column such that the biomolecules in the solution permeate the pores of the mineral oxide beads and are bound to the apatite crystals therein; and then flowing a second solution through the column to elute the biomolecules bound to the apatite crystals. In a fixed bed column the source liquid flows downwardly by gravity, while in a fluidized bed column the source liquid is propelled upwardly through the column. The biomolecules to be separated usually are polypeptides or nucleic acids. The composite sorbent is particularly useful for difficult protein separations, including antibody separation. It also is excellent for plasmids for the elimination of RNA and of open circles.

The following examples relate to specific embodiments within the scope of the present invention, but are not limiting.

EXAMPLE 1

Preparation of Zirconia Particles by Sol-gel

A silica sol is prepared by mixing sequentially and progressively 150 ml of sodium silicate 35% with 200 ml of water and 100 ml of water and 100 ml of glacial acetic acid. Dry solid irregular zirconia powder (350 mg of 0.3 to 3 $\mu$m size) is dispersed in this suspension. Cerium oxide (10 g) and cerium nitrate (10 g) are then added under vigorous stirring. Under the above conditions the gelation process occurs at ambient temperature within 15 to 60 minutes.

After complete gelation, which takes a few hours, the gel is divided into small pieces by press-filtering it through a $200\mu$ sieve. The particles are suspended in clear water and recovered by filtration, washed and then dried at 80° C. under an air stream.

The silica gel that entraps the solid zirconia and ceria composite microparticles is progressively dehydrated. At this point, the particles are soft and show only very modest porosity. Then, the particles are fired at 1300° C. for 2 hours. Under these conditions, the silica gel is totally dehydrated and shrinks to such an extent that it forms a continuous layer around the solid sub-particles. The void between subparticles constitutes the macroporosity.

After this treatment, the final pore volume represents more than 50% of the whole porous particle volume. The density of the dry irregular particles is about 2.1 g/cm³. After cooling, the beads do not show any cracks due to volume variation of mineral crystalline forms.

EXAMPLE 2

Preparation of Zirconia Particles by Suspension Polymerization

A silica sol is prepared by mixing sequentially and progressively 150 ml of sodium silicate 35% with 200 ml of water and 100 ml of water and 100 ml of glacial acetic acid. Dry solid irregular zirconia powder (350 mg of 0.3 to 3 $\mu$m size) is dispersed in this suspension. Cerium oxide (10 g) and cerium nitrate (10 g) are then added under vigorous stirring.

The resulting homogeneous suspension is slowly poured in an agitated paraffin oil bath containing 2% sorbitan sesquioleate and dispersed as small droplets. The suspension is heated at 80° C. while stirring. Under these conditions, the gelation process occurs at ambient temperature within 15 to 30 minutes.

The beads of a diameter ranging from 10 to 500 $\mu$m comprise a silica hydrogel trapped within its network solid microparticles of preformed zirconia and ceria. They are recovered by filtration, washed, and dried at 80° C. under an air stream. The gel is progressively dehydrated and acts as a binder for solid zirconia and ceria composite microparticles. The beads are then fired at 1300° C. for 2 hours, to singer bead subparticles with minimal pore volume reduction. After this treatment, the final pore volume represents more than 50% of the total bead volume. The density of the dry beads is about 2.1 g/cm³. After cooling, the beads do not show any cracks due to volume variation of mineral crystalline forms.

EXAMPLE 3

Preparation of Zirconia Beads by Spray Drying

A solution is prepared by mixing 231 g of zirconium nitrate and 143.6 g of yttrium nitrate in 1000 ml of distilled water. Yttrium oxide (144 g) and zirconia powder (752 g of 0.3 to 3 μm size) are added under gentle stirring to prevent the introduction of air bubbles.

The suspension is then injected into a vertical drying chamber through an atomization device, such as a revolving disk, a spray nozzle, or an ultrasonic nebulizer, together with a hot gas stream, preferably air or nitrogen. The hot gas stream causes rapid evaporation of water from the microdroplets. The gas is typically injected at 300–350° C. and exits the dryer at a temperature slightly above 100° C. Microparticles of original mineral oxides are consolidated into individual aggregates of spherical shape. Dry microbeads are then fired at a temperature close to the melting temperature of the zirconium oxide to irreversibly consolidate the network. After cooling, the beads do not show any cracks due to volume variation of mineral crystalline forms. This operation results in the formation of stable beads with a large pore volume that exceeds 50% of the bead volume.

EXAMPLE 4

Preparation of Hydroxyapatite Filled Zirconia Beads

The beads from Example 3 are washed with a 1M solution of phosphoric acid to eliminate impurities and then incubated with two volumes of 1M monopotassium phosphate overnight at room temperature under occasional shaking. The treated beads are then washed with water until neutral pH and dried under vacuum at 60–80° C. to eliminate all residual water. The pore volume of the dry beads is determined according to well-known methods.

A solution of calcium chloride is prepared by solubilizing 74 g of $CaCl_2 2H_2O$ in 500 ml of distilled water (final volume). The dry beads of treated zirconia are mixed with one pore volume of the solution of calcium chloride. After 30–60 minutes mixing, to ensure a good penetration of the solution into the pores of the mineral material, the beads are dried again, as above.

A solution of disodium phosphate is prepared by solubilizing 180 g of $Na_2HPO_4.12H_2O$ in 500 ml water (final volume). The dried beads are mixed with one pore volume of the solution, and the mixture again is thoroughly shaken for 30–60 minutes to ensure good penetration. The temperature is kept at 25–40° C.; and the material is left overnight.

The material then is mixed with a large volume of water and washed several times with water until elimination of the excess calcium ions (no precipitation of $Ca(OH)_2$ with NaOH should occur). The washed material is added to several volumes (at least 10) of sodium hydroxide at a concentration of 0.5M. The suspension is then brought to 95–100° C. for one hour and left overnight, during which time the temperature decreases to room temperature.

The treated material is again extensively washed with water and mixed with a solution of 3 g/l of disodium phosphate. The pH is adjusted to 6.8 and the suspension heated to 95–100° C. for about 20 minutes. The resulting material is finally washed with water and stored in a phosphate buffer at neutral pH containing 1M sodium chloride and 20% ethanol.

The present invention provides a novel composite adsorbent, methods of use and manufacture. While specific examples have been provided, the above description is illustrative and not restrictive. Any one or more of the features of the previously described embodiments can be combined in any manner with one or more features of any other embodiments in the present invention. Furthermore, many variations of the invention will be become apparent to those skilled in the art upon review of the specification. The scope of the invention should, therefore, be determined not with reference to the above description, but instead should be determined with reference to the appended claims along with the their full scope of equivalents.

All publication and patent documents cited in this application are incorporated by reference in their entirety for all purposed to the same extent as if each individual publication or patent document were so individually denoted. By their citation of various references in this document, Applicants do not admit any particular reference is "prior art" to their "invention."

What is claimed is:

1. A composite chromatography sorbent comprising:
   porous mineral oxide beads that have a pore volume which exceeds about 10% of the bead volume and an average pore diameter of at least about 500 Å, wherein the pores of the beads contain apatite crystals which have been formed within the pores of the beads by solutions that are allowed to penetrate the pores.

2. The composite chromatography sorbent of claim 1, wherein the mineral oxide is selected from the group consisting of alumina, titania, hafnia, silica, zirconia and mixtures thereof.

3. The composite chromatography sorbent of claim 1, wherein the mineral oxide is selected from the group consisting of zirconia, titania and hafnia, and wherein the pore volume is between about 30% and about 60% of the bead volume.

4. The composite chromatography sorbent of claim 1, wherein the mineral oxide is silica, and wherein the pore volume is between about 40% and about 70% of the bead volume.

5. The composite chromatography sorbent of claim 1, wherein pore volume is between about 30% and about 70% of the bead volume.

6. The composite chromatography sorbent of claim 1, wherein the average pore diameter is between about 1000 Å and about 4000 Å.

7. The composite chromatography sorbent of claim 1, wherein the mineral is selected from the group consisting of zirconia, titania and hafnia, and wherein the average pore diameter is between about 1000 Å and about 3000 Å.

8. The composite chromatography sorbent of claim 1, wherein the mineral is silica, and wherein the average pore diameter is between about 2000 Å and about 5000 Å.

9. The composite chromatography sorbent of claim 1, wherein the beads are coated with a layer of a hydrophilic polymer.

10. The composite chromatography sorbent of claim 9, wherein the hydrophilic polymer is selected from the group consisting of polyoxyethylene, polyoxypropylene, cross-linked polysaccharides and vinyl polymers.

11. The composite chromatography sorbent of claim 1, wherein the apatite crystals comprise:
   (a) calcium ions; and
   (b) a metal ion or a metalloid ion.

12. The composite chromatography sorbent of claim 11, wherein the metal ion or metalloid ion is strontium, barium or fluoride.

13. The composite chromatography sorbent according to claim 1, wherein the apatite crystals are hydroxyapatite crystals.

14. The composite chromatography sorbent according to claim 1, wherein the apatite crystals are hydroxyapatite crystals and the mineral oxide is zirconia.

* * * * *